(12) United States Patent
Hai

(10) Patent No.: US 10,146,073 B2
(45) Date of Patent: Dec. 4, 2018

(54) MEASUREMENT METHOD FOR LIQUID CRYSTAL AZIMUTHAL ANGLE OF LIQUID CRYSTAL PANEL AND MEASUREMENT DEVICE

(71) Applicant: Shenzhen China Star Optoelectronics Technology Co., Ltd., Shenzhen, Guangdong (CN)

(72) Inventor: Bo Hai, Guangdong (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 193 days.

(21) Appl. No.: 15/113,539

(22) PCT Filed: May 10, 2016

(86) PCT No.: PCT/CN2016/081508
§ 371 (c)(1),
(2) Date: Jul. 22, 2016

(87) PCT Pub. No.: WO2017/181451
PCT Pub. Date: Oct. 26, 2017

(65) Prior Publication Data
US 2018/0107033 A1    Apr. 19, 2018

(30) Foreign Application Priority Data
Apr. 19, 2016 (CN) .......................... 2016 1 0244376

(51) Int. Cl.
*G02F 1/13* (2006.01)
*G01B 11/26* (2006.01)
(Continued)

(52) U.S. Cl.
CPC ............ *G02F 1/1309* (2013.01); *G01B 11/26* (2013.01); *G01N 21/59* (2013.01); *G02F 1/13* (2013.01);
(Continued)

(58) Field of Classification Search
CPC ...... G09G 3/006; G01M 11/00; G01M 11/02; G01M 11/0207; G01N 2021/8477;
(Continued)

(56) References Cited

U.S. PATENT DOCUMENTS 5,532,823 A     7/1996 Fukui et al.
6,300,954 B1 * 10/2001 Sato .......................... G01J 4/04
                                                          349/187
(Continued)

FOREIGN PATENT DOCUMENTS

CN         101178488 A    5/2008
CN         101762891 A    6/2010
(Continued)

*Primary Examiner* — Gordon J Stock, Jr.
(74) *Attorney, Agent, or Firm* — Andrew C. Cheng

(57) ABSTRACT

A measurement method for a liquid crystal azimuthal angle of a liquid crystal panel and a measurement device are disclosed. The liquid crystal panel includes an upper polarization film, a lower polarization film disposed oppositely and liquid crystal molecules disposed there between. The method includes: when absorption axes of the upper and the lower polarization films are disposed as 0 degree and 90 degrees with respect to a horizontal direction, and are perpendicular to each other, measuring a first transmittance; when absorption axes of the upper and the lower polarization films are disposed as 45 degrees and 135 degrees with respect to the horizontal direction, and are perpendicular to each other, measuring a second transmittance; calculating to obtain the liquid crystal azimuthal angle of the liquid crystal panel according to the first transmittance and second transmittance. The present invention can measure the liquid crystal azimuthal angle quickly, simply, and effectively.

8 Claims, 2 Drawing Sheets

(51) Int. Cl.
*G09G 3/00* (2006.01)
*G01N 21/59* (2006.01)
*G01N 21/95* (2006.01)
*G01N 21/84* (2006.01)

(52) U.S. Cl.
CPC ..... *G09G 3/006* (2013.01); *G01N 2021/8477* (2013.01); *G01N 2021/9513* (2013.01)

(58) Field of Classification Search
CPC ... G01N 2021/8472; G01N 2021/8438; G01N 2021/9513; G01N 21/59; G01B 11/26; G02F 1/13; G02F 1/1306; G02F 1/1309
See application file for complete search history.

(56) References Cited

U.S. PATENT DOCUMENTS

| | | | | |
|---|---|---|---|---|
| 6,633,358 B1* | 10/2003 | Kwok | ............... | G01N 21/21 349/136 |
| 6,822,737 B2* | 11/2004 | Kurata | ............... | G02F 1/1309 356/364 |
| 7,202,950 B2* | 4/2007 | Shribak | ............... | G01J 4/00 356/364 |
| 7,477,387 B2* | 1/2009 | Saitoh | ............... | G01N 21/21 356/364 |
| 7,760,300 B2* | 7/2010 | Ham | ............... | G02F 1/1337 349/123 |
| 7,808,637 B2* | 10/2010 | Smith | ............... | G01B 11/0641 356/367 |
| 7,830,511 B2* | 11/2010 | Ham | ............... | G01N 21/23 250/225 |
| 2008/0285014 A1 | 11/2008 | Lo et al. | | |
| 2011/0096254 A1* | 4/2011 | Ikeda | ............... | G02F 1/13306 349/33 |
| 2014/0204318 A1 | 7/2014 | Kang et al. | | |

FOREIGN PATENT DOCUMENTS

| | | |
|---|---|---|
| CN | 102053398 A | 5/2011 |
| JP | 2005227019 A | 8/2005 |

* cited by examiner

MEASUREMENT METHOD FOR LIQUID CRYSTAL AZIMUTHAL ANGLE OF LIQUID CRYSTAL PANEL AND MEASUREMENT DEVICE

BACKGROUND OF THE INVENTION

1. Field of the Invention

The present invention relates to a liquid crystal display field, and more particularly to a measurement method for a liquid crystal azimuthal angle of a liquid crystal panel and a measurement device.

2. Description of Related Art

Along with the population and market expanding of the liquid crystal display, in many choices, the user has higher and higher demand for the performance of the liquid crystal display such as the transmittance and viewing angle of the liquid crystal molecules.

In the conventional art, in order to increase the transmittance of the liquid crystal molecules, generally, adjusting the azimuthal angle of the liquid crystal molecules is adopted such as disposing an azimuthal angle of an absorption axis of the polarization film and a long axis of the liquid crystal molecules to be 45 degrees. However, when increasing the transmittance of the liquid crystal molecules, the viewing angle should also be increased. At this time, the liquid crystal display is designed to be 4-domains or 8-domains. Therefore, an edge problem of the domains in the pixel is generated. That is, the liquid crystal azimuthal angle around the above structure is not 45 degrees as preset. Accordingly, the actual transmittance is far below a preset value. Because of the difference between the preset value and the actual value, a vision loss is generated. Besides, in another method, in order to increase the viewing angle, a situation that the liquid crystal azimuthal angle is not set as 45 degrees is existed. For example, in the continuous pinwheel alignment (CPA) technology, each pixel has a square electrode having rounded corners. When a voltage is applied on the electrode, a diagonal electric field drives the liquid crystal molecules to be aligned to the center of the electrode such that the liquid crystal molecules are faced toward the center of the electrode to be arranged as a radical firework. At this time, the liquid crystal azimuthal angle is not 45 degrees. Although the viewing angle is improved, the transmittance of the liquid crystal molecules is greatly lost.

SUMMARY OF THE INVENTION

The main technology problem solved by the present invention is to provide a measurement method for a liquid crystal azimuthal angle of a liquid crystal panel and a measurement device, which can measure the liquid crystal azimuthal angle quickly, simply, and effectively.

A technology solution adopted by the present invention is: providing a measurement method for a liquid crystal azimuthal angle of a liquid crystal panel, the liquid crystal panel includes an upper polarization film, a lower polarization film opposite to the upper polarization film and liquid crystal molecules disposed between the upper polarization film and the lower polarization film, and the method comprises:

when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group;

when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group;

according to at least one of the first transmittance and the second transmittance and an equation (1): $Tr=\frac{1}{2} \sin^2(2\theta) \sin^2(\pi \Delta ND/\lambda)$, calculating to obtain a liquid crystal azimuthal angle, wherein, Tr is the first transmittance or the second transmittance, $\theta$ is the liquid crystal azimuthal angle; $\Delta ND$ is phase retardation, $\lambda$ is a wavelength; and when measuring the first transmittance and the second transmittance, the liquid crystal panel displays a largest gray level value.

Wherein, the step of according to at least one of the first transmittance and the second transmittance and an equation (1): $Tr=\frac{1}{2} \sin^2(2\theta)\sin^2(\pi \Delta ND/\lambda)$, calculating to obtain a liquid crystal azimuthal angle comprises:

from the equation (1) and the first transmittance to obtain an equation (2): $Tr1=\frac{1}{2} \sin^2 2(45°\pm x)\sin^2(\pi \Delta ND/\lambda)$;

from the equation (1) and the second transmittance to obtain an equation (3): $Tr2=\frac{1}{2} \sin^2 2(\pm x)\sin^2(\pi \Delta ND/\lambda)$; and dividing the equation (2) by the equation (3), calculating to obtain the x;

wherein, x is an angle value of the liquid crystal azimuthal angle deviated from 45 degrees, the Tr1 is the first transmittance, and the Tr2 is the second transmittance.

Wherein, the liquid crystal panel includes one of a flexible screen liquid crystal panel and a rigid screen liquid crystal panel.

In order to solve the above technology problem, a technology solution adopted by the present invention is: providing another measurement method for a liquid crystal azimuthal angle of a liquid crystal panel, the liquid crystal panel includes an upper polarization film, a lower polarization film opposite to the upper polarization film and liquid crystal molecules disposed between the upper polarization film and the lower polarization film, and the method comprises:

when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group;

when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group; and calculating to obtain the liquid crystal azimuthal angle of the liquid crystal panel according to the first transmittance and the second transmittance.

Wherein, the step of calculating to obtain the liquid crystal azimuthal angle of the liquid crystal panel according to the first transmittance and the second transmittance comprises:

according to at least one of the first transmittance and the second transmittance and an equation (1): $Tr=½ \sin^2(2\theta)\sin^2(\pi\Delta ND/\lambda)$, calculating to obtain a liquid crystal azimuthal angle, wherein, Tr is the first transmittance or the second transmittance, $\theta$ is the liquid crystal azimuthal angle; $\Delta ND$ is phase retardation, $\lambda$ is a wavelength.

Wherein, the step of according to at least one of the first transmittance and the second transmittance and an equation (1): $Tr=½ \sin^2(2\theta)\sin^2(\pi\Delta ND/\lambda)$, calculating to obtain a liquid crystal azimuthal angle comprises:

from the equation (1) and the first transmittance to obtain an equation (2): $Tr1=½ \sin^2 2 (45°±x)\sin^2(\pi\Delta ND/\lambda)$;

from the equation (1) and the second transmittance to obtain an equation (3): $Tr2=½ \sin^2 2 (±x)\sin^2(\pi\Delta ND/\lambda)$; and dividing the equation (2) by the equation (3), calculating to obtain the x;

wherein, x is an angle value of the liquid crystal azimuthal angle deviated from 45 degrees, the Tr1 is the first transmittance, and the Tr2 is the second transmittance.

Wherein, when measuring the first transmittance and the second transmittance, the liquid crystal panel displays a largest gray level value.

Wherein, the liquid crystal panel includes one of a flexible screen liquid crystal panel and a rigid screen liquid crystal panel.

In order to solve the above technology problem, another technology solution adopted by the present invention is: providing a measurement device for a liquid crystal azimuthal angle of a liquid crystal panel, the liquid crystal panel includes an upper polarization film, a lower polarization film opposite to the upper polarization film and liquid crystal molecules disposed between the upper polarization film and the lower polarization film, and the measurement device comprises:

a first transmittance measurement module used for when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group;

a second transmittance measurement module used for when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group; and a liquid crystal azimuthal angle calculation module used for calculating the liquid crystal azimuthal angle of the liquid crystal panel according to the first transmittance and the second transmittance.

Wherein, the liquid crystal azimuthal angle calculation module is used for calculating to obtain the liquid crystal azimuthal angle according to at least one of the first transmittance and the second transmittance and an equation (1): $Tr=½ \sin^2(2\theta)\sin^2 (\pi\Delta ND/\lambda)$, wherein, Tr is the first transmittance or the second transmittance, $\theta$ is the liquid crystal azimuthal angle; $\Delta ND$ is phase retardation, $\lambda$ is a wavelength.

Wherein, the liquid crystal azimuthal angle calculation module is used for:

from the equation (1) and the first transmittance to obtain an equation (2): $Tr1=½ \sin^2 2 (45°±x)\sin^2(\pi\Delta ND/\lambda)$;

from the equation (1) and the second transmittance to obtain an equation (3): $Tr2=½ \sin^2 2 (±x)\sin^2(\pi\Delta ND/\lambda)$; and dividing the equation (2) by the equation (3), calculating to obtain the x;

wherein, x is an angle value of the liquid crystal azimuthal angle deviated from 45 degrees, the Tr1 is the first transmittance, and the Tr2 is the second transmittance.

Wherein, when measuring the first transmittance and the second transmittance, the liquid crystal panel displays a largest gray level value.

Wherein, the liquid crystal panel includes one of a flexible screen liquid crystal panel and a rigid screen liquid crystal panel.

The beneficial effects of the present invention is: comparing to the conventional art, in the present embodiment, when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group; when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group; and finally calculating to obtain the liquid crystal azimuthal angle of the liquid crystal panel according to the first transmittance and the second transmittance. Through the above method, the present invention can measure the liquid crystal azimuthal angle accurately, evaluating the transmittance of the liquid crystal panel accurately and providing a data base for adjusting the liquid crystal azimuthal angle. Besides, in the measurement method of the present invention, only required to measure the panel two times, the number of measuring is few, the measurement method is simple, the measurement cost is low and the application range is wide.

DETAILED DESCRIPTION OF THE PREFERRED EMBODIMENT

Figure 1:
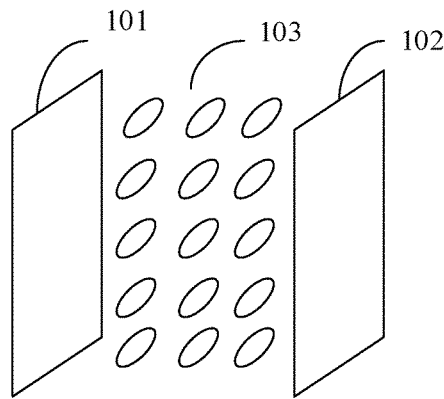
FIG. 1 is a schematic diagram of a liquid crystal panel of an embodiment of the present invention.

With reference to FIG. 1, and FIG. 1 is a schematic diagram of a liquid crystal panel of an embodiment of the present invention. The liquid crystal panel includes an upper polarization film 101, a lower polarization film 102 disposed opposite to the upper polarization film and liquid crystal molecules 103 disposed between the upper polarization film 101 and the lower polarization film 102. The liquid crystal panel includes one of a VA type liquid crystal panel with flexible screen or an IPS type liquid crystal panel with rigid screen.

In a general condition, without applying a voltage, the VA type liquid crystal panel with flexible screen or the IPS type liquid crystal panel with rigid screen is under a normally black state. Specifically, an absorption axis of the upper polarization film 101 and an absorption axis of the lower polarization film are perpendicular to each other. When an incident light pass through the lower polarization film 102, the incident light become a linearly polarized light, the polarization direction of the incident light is consistent with a penetration direction of the lower polarization film 102. Because no voltage is applied, when the linearly polarized light pass through the liquid crystal molecules 103, the polarization direction will not be changed by the liquid crystal molecules. When the linearly polarized light pass through the upper polarization film 101, the linearly polarized light will be absorbed so that the liquid crystal panel displays a black state.

When the liquid crystal panel is applied with a voltage, the liquid crystal molecules 103 are deflected along an alignment direction. Because the linearly polarized light will be refracted by the liquid crystal molecules 103, when the linearly polarized light pass through the liquid crystal molecules 103, the light is split into two light beams, and the propagation velocity of the two light beams is different. When entering to the upper polarization film 101, one of the two light beams which is in parallel with the penetration direction of the upper polarization film 101 can pass through. At this time, the liquid crystal panel performs a bright state.

Although, when applying a voltage, the liquid crystal panel performs a bright state, however, not every liquid crystal panel is under a state having a highest transmittance, and the transmittance is a very important index of a liquid crystal panel.

Figure 2:
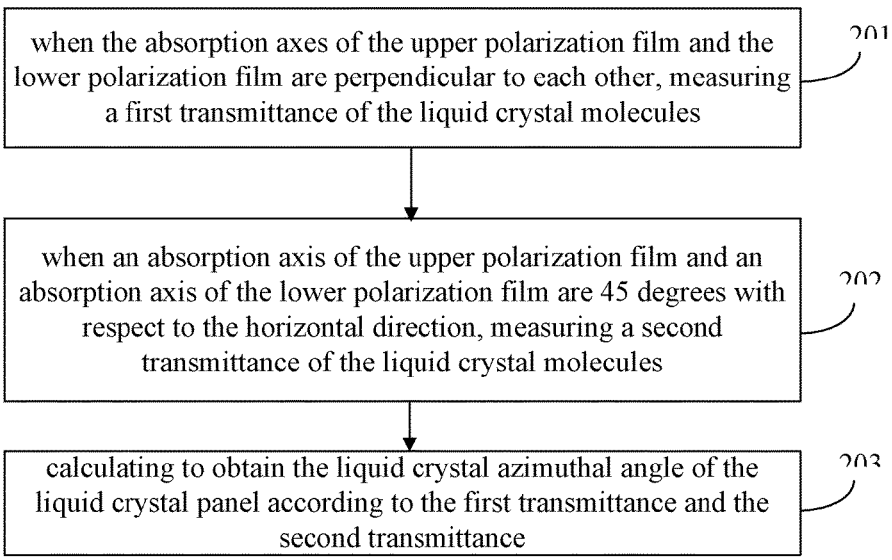
FIG. 2 is a flow chart of a measurement method for a liquid crystal azimuthal angle of a liquid crystal panel of an embodiment of the present invention.

With reference to FIG. 2, and FIG. 2 is a flow chart of a measurement method for a liquid crystal azimuthal angle of a liquid crystal panel of an embodiment of the present invention. Wherein, the liquid crystal azimuthal angle is an azimuthal angle between an absorption axis of the upper polarization film 101 and a long axis of the liquid crystal molecule 103 or between an absorption axis of the lower polarization film 102 and the long axis of the liquid crystal molecule 103.

As shown in FIG. 2, the measurement method for liquid crystal azimuthal angle of the present embodiment includes following steps:

201: when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group.

Specifically, the present embodiment can select that the absorption axis of the upper polarization film 101 is 0 degree with respect to the horizontal direction, and the absorption axis of the lower polarization film 102 is 90 degree with respect to the horizontal direction. It should be noted that the upper polarization film 101 and the lower polarization film 102 here are not limited, the only requirement is that the absorption axis of one of the two polarization films is 0 degree with respect to the horizontal direction, and the absorption axis of the other of the two polarization film is 90 degrees with respect to the horizontal direction.

Then, when the display panel displays a largest gray level value, measuring the first transmittance, wherein, the largest gray level value is 255.

As shown in Table 1, Table 1 is the related data obtained by measuring the first transmittance under some parameters.

TABLE 1

| Absorption axes of the first and second polarization films are perpendicular to each other | | | |
|---|---|---|---|
| W | 0.26 | 0.275 | 317 |
| R | 0.638 | 0.341 | 47.7 |
| G | 0.305 | 0.61 | 238.7 |
| B | 0.146 | 0.05 | 31.5 |
| D | 0.222 | 0.188 | 0.07 |
| NTSC | | | 72.50% |
| CR | | | 4529 |

Wherein, W is white brightness, R is red brightness, G is green brightness, B is blue brightness, B is black brightness, and NTSC is a gamut.

As shown in table. 1, when the absorption axes of the upper and lower polarization films are disposed as 0 degree and 90 degrees with respect to the horizontal direction, and are perpendicular to each other, under some parameters, the white brightness is 317, and a backlight brightness is 4662. The first transmittance=the white brightness/the backlight brightness such that the first transmittance is 6.8%.

202: when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group.

Specifically, the present embodiment can select that the absorption axis of the upper polarization film 101 is 45 degrees with respect to the horizontal direction, and the absorption axis of the lower polarization film 102 is 135 degrees with respect to the horizontal direction. It should be noted that the upper polarization film 101 and the lower polarization film 102 here are not limited, the only requirement is that the absorption axis of one of the two polarization films is 45 degrees with respect to the horizontal direction, and the absorption axis of the other of the two polarization films is 135 degrees with respect to the horizontal direction.

Then, when the display panel displays a largest gray level value, measuring the second transmittance, wherein, the largest gray level value is 255.

In a specific embodiment, the upper polarization film 101 and the lower polarization film 102 used for measuring the first transmittance can be removed. Further selecting an absorption axis of an upper polarization film 101 with respect to the horizontal direction is 45 degrees and an absorption axis of a lower polarization film 102 with respect to the horizontal direction is 135 degrees. That is, the absorption axis of the upper polarization film 101 and the absorption axis of the lower polarization film 102 are orthogonal mutually. In a preferred embodiment, in order to obtain a more precise liquid crystal azimuthal angle, the two polarization films for measuring the first transmittance and the two polarization films for measuring the second transmittance can adopt polarization films having a same model number.

As shown in Table 2, Table 2 is the related data obtained by measuring the second transmittance under some parameters.

TABLE 2

Absorption axes of the upper and lower polarization films are 45 degrees with respect to the horizontal direction

| | | | |
|---|---|---|---|
| W | 0.265 | 0.286 | 61.7 |
| R | 0.631 | 0.338 | 9.2 |
| G | 0.304 | 0.607 | 46.6 |
| B | 0.417 | 0.05 | 5052 |
| D | 0.242 | 0.228 | 0.1 |
| NTSC | | | 70.90% |
| CR | | | 617 |

Wherein, W is white brightness, R is red brightness, G is green brightness, B is blue brightness, B is black brightness, and NTSC is a gamut.

As shown in table. 2, when absorption axes of the upper and lower polarization films are 45 degrees with respect to the horizontal direction, under some parameters, the white brightness is 61.7, and a backlight brightness is 4679. The second transmittance=the white brightness/the backlight brightness such that the second transmittance is 1.32%.

203: calculating to obtain the liquid crystal azimuthal angle of the liquid crystal panel according to the first transmittance and the second transmittance.

Figure 3:
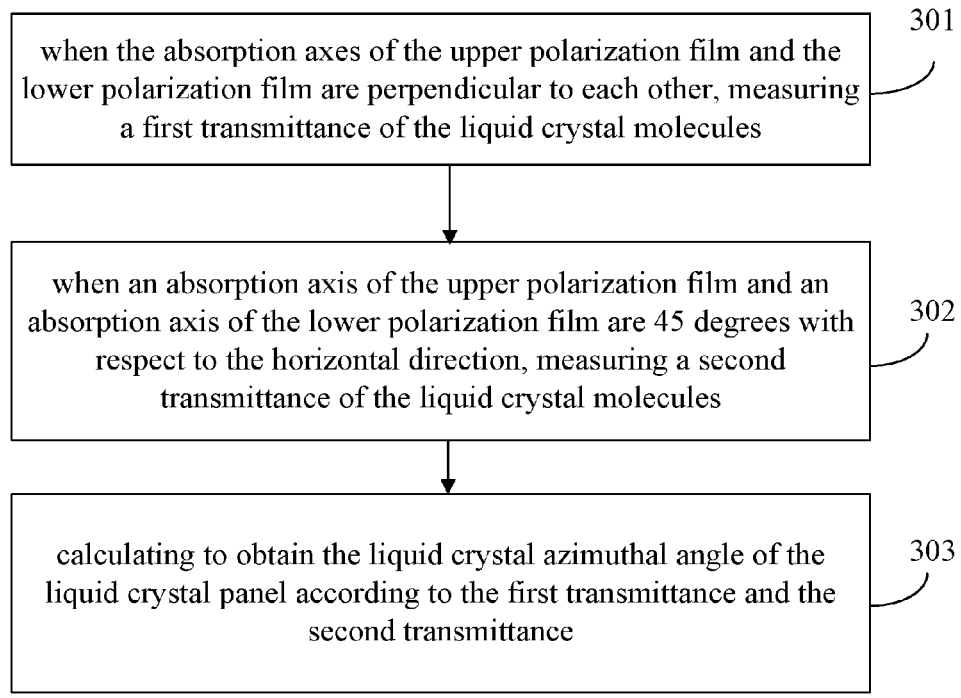
FIG. 3 is a flow chart of a measurement method for a liquid crystal azimuthal angle of a liquid crystal panel of another embodiment of the present invention.

Specifically, with reference to FIG. 3, and FIG. 3 is a flow chart of a measurement method for a liquid crystal azimuthal angle of a liquid crystal panel of another embodiment of the present invention. FIG. 3 is a specific embodiment of the measurement method shown in FIG. 2. Because the steps S301~302 are the same as the steps 201~202, no more repeating here.

Step 303: according to at least one of the first transmittance and the second transmittance and an equation (1): $Tr=\frac{1}{2}\sin^2(2\theta)\sin^2(\pi\Delta ND/\lambda)$, calculating to obtain a liquid crystal azimuthal angle, wherein, Tr is the first transmittance or the second transmittance, $\theta$ is the liquid crystal azimuthal angle; $\Delta ND$ is phase retardation, $\lambda$ is a wavelength.

Because when an azimuthal angle is 45 degrees, the transmittance is largest, in the present embodiment, a degree of an azimuthal angle that deviates from 45 degrees represents a liquid crystal azimuthal angle.

Specifically, assuming that the liquid crystal azimuthal angle is 45°±x, that is, the absorption axes of the upper polarization film 101 and the lower polarization film 102 are perpendicular mutually, the absorption axes with respect to the horizontal direction are respectively 0 degree and 90 degrees, from equation (1) and the first transmittance to obtain an equation (2):

$Tr1=\frac{1}{2}\sin^2 2(45°\pm x)\sin^2(\pi\Delta ND/\lambda)$; wherein, x is an angle value representing that the liquid crystal azimuthal angle deviated from 45 degrees. Because $\sin^2 2(45°+x)=\sin^2 2(45°-x)$, 45°+x represents that the liquid crystal azimuthal angle is greater than 45 degrees by x degrees, 45°-x represents that the liquid crystal azimuthal angle is less than 45 degrees by x degrees. In either case, x all represents an angle value that the liquid crystal azimuthal angle deviated from 45 degrees.

Tr1 is the first transmittance, $\theta$ is the liquid crystal azimuthal angle; $\Delta ND$ is phase retardation, $\lambda$ is a wavelength.

Because $\sin^2 2(45°+x)=\sin^2 2(45°-x)$, 45°+x represents that the liquid crystal azimuthal angle is greater than 45 degrees by x degrees, 45°-x represents that the liquid crystal azimuthal angle is less than 45 degrees by x degrees. In either case, x all represents an angle value that the liquid crystal azimuthal angle deviated from 45 degrees.

When absorption axes of the upper polarization film and the lower polarization film are 45 degrees with respect to the horizontal direction, a liquid crystal azimuthal angle between a long axis of the liquid crystal molecules 103 and the upper polarization film 101 or the lower polarization film 102 is ±x, wherein, x is angle value of the liquid crystal azimuthal angle deviated from 45 degrees, and obtaining an equation (3) from the equation (1) and the second transmittance:

$Tr2=\frac{1}{2}\sin^2 2(\pm x)\sin^2(\pi\Delta ND/\lambda)$; wherein, Tr2 is the second transmittance obtained by measuring.

Dividing the equation (2) by the equation (3), calculating to obtain the x, as shown as following:

$Tr1/Tr2=[\frac{1}{2}\sin^2 2(45°\pm x)\sin^2(\pi\Delta ND/\lambda)]/[\frac{1}{2}\sin^2 2(\pm x)\sin^2(\pi\Delta ND/\lambda)]$ Because the transmittance Tr is an integration result of Tr of each wavelength, in the calculation process, the term $\sin^2(\pi\Delta ND/\lambda)$ of each wavelength is canceled out so that, $Tr1/Tr2=[\sin^2 2(45°\pm x)]/[\sin^2 2(\pm x)]$ According to the trigonometric equations, $\sin^2 2(45°\pm x)=\sin^2(90°\pm 2x)=\cos^2(\pm 2x)$ so that, $Tr1/Tr2=[\cos^2(\pm 2x)]/[\sin^2(\pm x)]=\cot^2(\pm 2x)$, For example, inputting the first transmittance 6.8% and the second transmittance 1.32% obtained by the steps 201~202 and the steps 301~302, obtaining.

$Tr1/Tr2=\cot^2(\pm 2x)=6.8\%/1.32\%=5.152$.

Solving the equation to obtain that x=11.9 degrees, that is, under the current parameters, the liquid crystal azimuthal angle is 11.9 degrees deviated from 45 degrees.

In another embodiment, according to the measured first transmittance or the second transmittance and combining with the equation (2): $Tr1=\frac{1}{2}\sin^2 2(45°\pm x)\sin^2(\pi\Delta ND/\lambda)$, or equation (3): $Tr2=\frac{1}{2}\sin^2 2(\pm x)\sin^2(\pi\Delta ND/\lambda)$, In the premise that D and $\lambda$ are known, the angle value x of the liquid crystal azimuthal angle deviated from 45 degrees can be obtained individually. The difference is that through the division of the first transmittance and the second transmittance, the term $\sin^2(\pi\Delta ND/\lambda)$ that may generate an error can be canceled out in order to further increase the precision of measuring the liquid crystal azimuthal angle.

Comparing to the conventional art, in the present embodiment, when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group; when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group; and finally calculating to obtain the liquid crystal azimuthal angle of the liquid crystal panel according to the first transmittance and the second transmittance. Through the above method, the present invention can measure the liquid crystal azimuthal angle accurately, evaluating the transmittance of the liquid crystal panel accurately and providing a data base for adjusting the liquid crystal azimuthal angle. Besides, in the measurement method of the present invention, only required to measure the panel two times, the number of measuring is few, the measurement method is simple, the measurement cost is low and the application range is wide.

Figure 4:
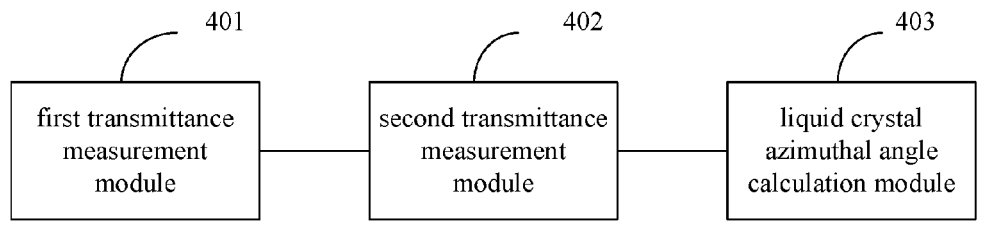
FIG. 4 is a schematic diagram of a measurement device for a liquid crystal azimuthal angle of a liquid crystal panel of the present invention.

With reference to FIG. 4, and FIG. 4 is a schematic diagram of a measurement device for a liquid crystal azimuthal angle of a liquid crystal panel of the present invention. Wherein, the liquid crystal panel includes an upper polarization film, a lower polarization film disposed opposite to the upper polarization film and liquid crystal molecules disposed between the upper polarization film and the lower polarization film. As shown in FIG. 4, the measurement device of the present embodiment includes a first transmittance measurement module 401 and a second transmittance measurement module 402 and a liquid crystal azimuthal angle calculation module 403.

Wherein, the liquid crystal azimuthal angle is an azimuthal angle between an absorption axis of the upper polarization film and a long axis of the liquid crystal molecule or between an absorption axis of the lower polarization film and a long axis of the liquid crystal molecule.

The first transmittance measurement module 401 is used for when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group.

Specifically, the first transmittance measurement module 401 can select that the absorption axis of the upper polarization film 101 is 0 degree with respect to the horizontal direction, and the absorption axis of the lower polarization film 102 is 90 degrees with respect to the horizontal direction. It should be noted that the upper polarization film 101 and the lower polarization film 102 here are not limited, the only requirement is that the absorption axis of one of the two polarization films is 0 degree with respect to the horizontal direction, and the absorption axis of the other of the two polarization film is 90 degrees with respect to the horizontal direction.

Then, when the display panel displays a largest gray level value, measuring the first transmittance, wherein, the largest gray level value is 255.

As shown in Table 3, Table 3 is the related data obtained by the first transmittance measurement module 401 when measuring the first transmittance under some parameters.

Wherein, W is white brightness, R is red brightness, G is green brightness, B is blue brightness, B is black brightness, and NTSC is a gamut.

As shown in table. 3, when absorption axes of the upper and lower polarization films are disposed as o degree and 90 degrees with respect to the horizontal direction, and are perpendicular to each other, under some parameters, the white brightness is 317, and a backlight brightness is 4662. The first transmittance=the white brightness/the backlight brightness such that the first transmittance is 6.8%.

The second transmittance measurement module 402 is used for when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group.

Specifically, the present embodiment can select that the absorption axis of the upper polarization film 101 is 45 degrees with respect to the horizontal direction, and the absorption axis of the lower polarization film 102 is 135 degrees with respect to the horizontal direction. It should be noted that the upper polarization film 101 and the lower polarization film 102 here are not limited, the only requirement is that the absorption axis of one of the two polarization films is 45 degrees with respect to the horizontal direction, and the absorption axis of the other of the two polarization films is 135 degrees with respect to the horizontal direction Then, when the display panel displays a largest gray level value, the second transmittance measurement module 402 measures the second transmittance, wherein, the largest gray level value is 255.

In a specific embodiment, the upper polarization film 101 and the lower polarization film 102 used for measuring the first transmittance can be removed. Further selecting an absorption axis of an upper polarization film 101 with respect to the horizontal direction is 45 degrees and an absorption axis of a lower polarization film 102 with respect to the horizontal direction is 135 degrees. That is, the absorption axis of the upper polarization film 101 and the absorption axis of the lower polarization film 102 are orthogonal mutually. In a preferred embodiment, in order to obtain a more precise liquid crystal azimuthal angle, the two polarization films for measuring the first transmittance and the two polarization films for measuring the second transmittance can adopt polarization films having a same model number.

As shown in Table 4, Table 4 the related data obtained by the second transmittance measurement module 402 when measuring the second transmittance under some parameters.

TABLE 3 the absorption axes of the upper polarization film and the lower polarization film are perpendicular to each other

| | | | |
|---|---|---|---|
| W | 0.26 | 0.275 | 317 |
| R | 0.638 | 0.341 | 47.7 |
| G | 0.305 | 0.61 | 238.7 |
| B | 0.146 | 0.05 | 31.5 |
| D | 0.222 | 0.188 | 0.07 |
| NTSC | | | 72.50% |
| CR | | | 4529 |

TABLE 4

Absorption axes of the upper and lower polarization films are 45 degrees with respect to the horizontal direction

| | | | |
|---|---|---|---|
| W | 0.265 | 0.286 | 61.7 |
| R | 0.631 | 0.338 | 9.2 |
| G | 0.304 | 0.607 | 46.6 |
| B | 0.417 | 0.05 | 5052 |
| D | 0.242 | 0.228 | 0.1 |
| NTSC | | | 70.90% |
| CR | | | 617 |

Wherein, W is white brightness, R is red brightness, G is green brightness, B is blue brightness, B is black brightness, and NTSC is a gamut.

As shown in table. 4, when absorption axes of the upper and lower polarization films are 45 degrees with respect to the horizontal direction, under some parameters, the white brightness is 61.7, and a backlight brightness is 4679. The second transmittance=the white brightness/the backlight brightness such that the second transmittance is 1.32%.

The liquid crystal azimuthal angle calculation module 403 is used for calculating the liquid crystal azimuthal angle of the liquid crystal panel according to the first transmittance and the second transmittance.

Specifically, the liquid crystal azimuthal angle calculation module 403 calculates to obtain a liquid crystal azimuthal angle according to at least one of the first transmittance and the second transmittance and an equation (1): $Tr=\frac{1}{2}\sin^2(2\theta)\sin^2(\pi\Delta ND/\lambda)$, wherein, Tr is the first transmittance or the second transmittance, $\theta$ is the azimuthal angle; $\Delta ND$ is phase retardation, $\lambda$ is a wavelength.

Because when a liquid crystal azimuthal angle is 45 degrees, the transmittance is largest, in the present embodiment, a degree of a liquid crystal azimuthal angle that deviates from 45 degrees represents a liquid crystal azimuthal angle.

Specifically, assuming that the liquid crystal azimuthal angle is 45°±x, that is, the absorption axes of the upper polarization film 101 and the lower polarization film 102 are perpendicular mutually, the absorption axes with respect to the horizontal direction are respectively 0 degree and 90 degrees, from the equation (1) and the first transmittance to obtain an equation (2):

$Tr1=\frac{1}{2}\sin^2 2(45°\pm x)\sin^2(\pi\Delta ND/\lambda)$; wherein, x is an angle value representing that the liquid crystal azimuthal angle deviated from 45 degrees. Because $\sin^2 2(45°+x)=\sin^2 2(45°-x)$, 45°+x represents that the liquid crystal azimuthal angle is greater than 45 degrees by x degrees, 45°−x represents that the liquid crystal azimuthal angle is less than 45 degrees by x degrees. In either case, x all represents an angle value that the liquid crystal azimuthal angle deviated from 45 degrees.

Tr1 is the first transmittance, $\theta$ is the liquid crystal azimuthal angle; $\Delta ND$ is phase retardation, $\lambda$ is a wavelength.

Because $\sin^2 2(45°+x)=\sin^2 2(45°-x)$, 45°+x represents that the liquid crystal azimuthal angle is greater than 45 degrees by x degrees, 45°−x represents that the liquid crystal azimuthal angle is less than 45 degrees by x degrees. In either case, x all represents an angle value of the liquid crystal azimuthal angle deviated from 45 degrees.

When absorption axes of the upper polarization film and the lower polarization film are 45 degrees with respect to the horizontal direction, a liquid crystal azimuthal angle between a long axis of the liquid crystal molecules 103 and the upper polarization film 101 or the lower polarization film 102 is ±x, wherein, x is angle value of the liquid crystal azimuthal angle deviated from 45 degrees, and from the equation (1) and the second transmittance to obtain an equation (3):

$Tr2=\frac{1}{2}\sin^2 2(\pm x)\sin^2(\pi\Delta ND/\lambda)$; wherein, Tr2 is the second transmittance obtained by measuring.

Dividing the equation (2) by the equation (3), calculating to obtain the x, as shown as following:

$Tr1/Tr2=[\frac{1}{2}\sin^2 2(45°\pm x)\sin^2(\pi\Delta ND/\lambda)]/[\frac{1}{2}\sin^2 2(\pm x)\sin^2(\pi\Delta ND/\lambda)]$ Because the transmittance Tr is an integration results of Tr of each wavelength, in the calculation process, the term $\sin^2(\pi\Delta ND/\lambda)$ of each wavelength is canceled out so that, $Tr1/Tr2=[\sin^2 2(45°\pm x)]/[\sin^2 2(\pm x)]$ According to the trigonometric equations, $\sin^2 2(45°\pm x)=\sin^2(90°\pm 2x)=\cos^2(\pm 2x)$ so that, $Tr1/Tr2=[\cos^2(\pm 2x)]/[\sin^2(\pm x)]=\cot^2(\pm 2x)$, For example, inputting the first transmittance 6.8% and the second transmittance 1.32% obtained by the step 201~202 and the steps 301~302, obtaining.

$Tr1/Tr2=\cot^2(\pm 2x)=6.8\%/1.32\%=5.152$.

Solving the equation to obtain that x=11.9 degrees, that is, under the current parameters, the liquid crystal azimuthal angle is 11.9 degrees deviated from 45 degrees.

In another embodiment, according to the measured first transmittance or the second transmittance and combining with the equation (2): $Tr1=\frac{1}{2}\sin^2 2(45°+x)\sin^2(\pi\Delta ND/\lambda)$, or equation (3): $Tr2=\frac{1}{2}\sin^2 2(\pm x)\sin^2(\pi\Delta ND/\lambda)$, In the premise that D and $\lambda$ are known, the angle value x of the liquid crystal azimuthal angle deviated from 45 degrees can be obtained individually. The difference is that through the division of the first transmittance and the second transmittance, the term $\sin^2(\pi\Delta ND/\lambda)$ that may generate an error can be canceled out in order to further increase the precision of measuring the liquid crystal azimuthal angle.

Comparing to the conventional art, in the present embodiment, when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group; when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group; and finally calculating to obtain the liquid crystal azimuthal angle of the liquid crystal panel according to the first transmittance and the second transmittance. Through the above method, the present invention can measure the liquid crystal azimuthal angle accurately, evaluating the transmittance of the liquid crystal panel accurately and providing a data base for adjusting the liquid crystal azimuthal angle. Besides, in the measurement method of the present invention, only required to measure the panel two times, the number of measuring is few, the measurement method is simple, the measurement cost is low and the application range is wide.

The above embodiments of the present invention are not used to limit the claims of this invention. Any use of the content in the specification or in the drawings of the present invention which produces equivalent structures or equivalent processes, or directly or indirectly used in other related technical fields is still covered by the claims in the present invention.

What is claimed is:

1. A measurement method for a liquid crystal azimuthal angle of a liquid crystal panel, the liquid crystal panel includes an upper polarization film, a lower polarization film opposite to the upper polarization film and liquid crystal molecules disposed between the upper polarization film and the lower polarization film, and the method comprising:

when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group of 0 degree and 90 degrees;

when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group of 45 degrees and 135 degrees;

according to at least one of the first transmittance and the second transmittance and an equation (1): $Tr=\frac{1}{2} \sin^2(2\theta)\sin^2(\pi\Delta ND/\lambda)$, calculating to obtain a liquid crystal azimuthal angle, wherein, Tr is the first transmittance or the second transmittance, $\theta$ is the liquid crystal azimuthal angle; $\Delta ND$ is phase retardation, $\lambda$ is a wavelength; and when measuring the first transmittance and the second transmittance, the liquid crystal panel displays a largest gray level value.

2. The measurement method according to claim 1, wherein, the step of according to at least one of the first transmittance and the second transmittance and an equation (1): $Tr=\frac{1}{2} \sin^2(2\theta)\sin^2(\pi\Delta ND/\lambda)$, calculating to obtain a liquid crystal azimuthal angle comprises:

from the equation (1) and the first transmittance to obtain an equation (2): $Tr1=\frac{1}{2} \sin^2 2(45°\pm x)\sin^2(\pi\Delta ND/\lambda)$;

from the equation (1) and the second transmittance to obtain an equation (3): $Tr2=\frac{1}{2} \sin^2 2(\pm x)\sin^2(\pi\Delta ND/\lambda)$; and dividing the equation (2) by the equation (3), calculating to obtain the x;

wherein, x is an angle value of the liquid crystal azimuthal angle deviated from 45 degrees, the Tr1 is the first transmittance, and the Tr2 is the second transmittance.

3. The measurement method according to claim 1, wherein, the liquid crystal panel includes one of a flexible screen liquid crystal panel and a rigid screen liquid crystal panel.

4. A measurement method for a liquid crystal azimuthal angle of a liquid crystal panel, the liquid crystal panel includes an upper polarization film, a lower polarization film opposite to the upper polarization film and liquid crystal molecules disposed between the upper polarization film and the lower polarization film, and the method comprises:

when an absorption axis of the upper polarization film and an absorption axis of the lower polarization film are disposed as an angle group of 0 degree and 90 degrees with respect to a horizontal direction, and the absorption axes of the upper polarization film and the lower polarization film are perpendicular to each other, measuring a first transmittance of the liquid crystal molecules corresponding to the angle group of 0 degree and 90 degrees;

when an absorption axis of the upper polarization film and an absorption axis of the lower polarization film are disposed as an angle group of 45 degrees and 135 degrees with respect to the horizontal direction, and the absorption axes of the upper polarization film and the lower polarization film are perpendicular to each other, measuring a second transmittance of the liquid crystal molecules corresponding to the angle group of 45 degrees and 135 degrees; and calculating to obtain the liquid crystal azimuthal angle of the liquid crystal panel according to the first transmittance and the second transmittance.

5. The measurement method according to claim 4, wherein, when measuring the first transmittance and the second transmittance, the liquid crystal panel displays a largest gray level value.

6. The measurement method according to claim 4, wherein, the liquid crystal panel includes one of a flexible screen liquid crystal panel and a rigid screen liquid crystal panel.

7. The measurement method according to claim 4, wherein, the step of calculating to obtain the liquid crystal azimuthal angle of the liquid crystal panel according to the first transmittance and the second transmittance comprises:

according to at least one of the first transmittance and the second transmittance and an equation (1): $Tr=\frac{1}{2} \sin^2(2\theta)\sin^2(\pi\Delta ND/\lambda)$, calculating to obtain a liquid crystal azimuthal angle, wherein, Tr is the first transmittance or the second transmittance, $\theta$ is the liquid crystal azimuthal angle; $\Delta ND$ is phase retardation, $\lambda$ is a wavelength.

8. The measurement method according to claim 7, wherein, the step of according to at least one of the first transmittance and the second transmittance and an equation (1): $Tr=\frac{1}{2} \sin^2(2\theta)\sin^2(\pi\Delta ND/\lambda)$, calculating to obtain a liquid crystal azimuthal angle comprises:

from the equation (1) and the first transmittance to obtain an equation (2): $Tr1=\frac{1}{2} \sin^2 2(45°\pm x)\sin^2(\pi\Delta ND/\lambda)$;

from the equation (1) and the second transmittance to obtain an equation (3): $Tr2=\frac{1}{2} \sin^2 2(\pm x)\sin^2(\pi\Delta ND/\lambda)$; and dividing the equation (2) by the equation (3), calculating to obtain the x;

wherein, x is an angle value of the liquid crystal azimuthal angle deviated from 45 degrees, the Tr1 is the first transmittance, and the Tr2 is the second transmittance.

* * * * *